(12) United States Patent
Rapp

(10) Patent No.: US 7,943,371 B1
(45) Date of Patent: May 17, 2011

(54) SYSTEM AND TESTING BIOLOGICAL AND CHEMICAL AGENTS USING TWO OR MORE CARTRIDGES SIMULATING SYSTEMS IN THE BODY AND METHODS

(75) Inventor: Edward J. Rapp, Cleveland Heights, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 1222 days.

(21) Appl. No.: 11/546,704

(22) Filed: Oct. 12, 2006

(51) Int. Cl.
*C12M 1/12* (2006.01)
(52) U.S. Cl. .................................. 435/297.4
(58) Field of Classification Search ..... 435/297.2–297.4
See application file for complete search history.

(56) References Cited

U.S. PATENT DOCUMENTS

| 5,149,649 | A | * | 9/1992 | Miyamori et al. | 435/400 |
| 5,424,209 | A | * | 6/1995 | Kearney | 435/286.5 |
| 5,578,485 | A | | 11/1996 | Naughton et al. | |
| 6,022,742 | A | * | 2/2000 | Kopf | 435/383 |
| 6,127,141 | A | * | 10/2000 | Kopf | 435/41 |
| 6,667,172 | B2 | | 12/2003 | Janigro et al. | |
| 6,884,591 | B2 | | 4/2005 | Janigro et al. | |

OTHER PUBLICATIONS

University of Chicago medical center, trial begins for first artificial liver device using human cells, http://www.uchospitals.edu/news/1999/19990225-elad.html , Feb. 25, 1999.*
K.A. Stannes, J.F. Neumaier, T.J. Sexton, G.A. Grant, A. Emmi, D.O. Maris, D. Janigro; A New Model of the Blood-Brain Barrier: Co-Culture of Neuronal, Endothelial and Glial Cells Under Dynamic Conditions, NeuroReport, Lippincott, Williams & Watkins, USA, Dec. 16, 1999, vol. 10, No. 18; pp. 3725-3731.
D. Janigro, S.M. Leaman, & K.A. Stanness; Dynamic in vitro Modeling of the Blood-Brain Barrier: A Novel Tool for the Studies of Drug Delivery to the Brain, Pharmaceutical Science and Technology Today; Elsevier Science, USA, vol. 2, No. 1, Jan. 1, 1999, pp. 7-12(6).
L. Cucullo, M.S. McAllister, K.Kight, L. Krizanac-Bengez, M. Marroni, M.R. Mayberg, K.A. Stanness, D. Janigro; A New Dynamic in vitro Model for the Multidimentional Study of Astrocyte-Endothelial Cell Interactions at the Blood-Brain Barrier; Brain Research, Elsevier Science, USA, Jun. 27, 2002, vol. 951; pp. 243-254.

* cited by examiner

*Primary Examiner* — Walter D Griffin
*Assistant Examiner* — Shanta G Doe
(74) *Attorney, Agent, or Firm* — Brian M. Kolkowski

(57) ABSTRACT

The present invention relates to joining two or more cartridges containing cell or tissue cultures from different organs found in the human body in fluid connection. It includes a vitro method and system for testing chemicals and agents as they pass through organs other than the brain or combinations of body systems including the brain. It greatly enhances the ability for researchers to test a proposed chemical or agent on human cells and tissue prior to testing it in vivo. Often, it is found that chemicals or agents have different reactions when tested on a single organ in vitro or in animals, than it does in the human body.

14 Claims, 5 Drawing Sheets

SYSTEM AND TESTING BIOLOGICAL AND CHEMICAL AGENTS USING TWO OR MORE CARTRIDGES SIMULATING SYSTEMS IN THE BODY AND METHODS

BACKGROUND OF THE INVENTION

1. Field of the Invention

The present invention relates to joining two or more cartridges each containing different cell or tissue cultures in fluid connection.

2. Technical Background

The effect of an experimental drug or chemical in the human body is difficult to predict because of differences in blood composition, tissue binding, regional pH, and permeability of cell membranes. Ideally, a drug should enter the body, go directly to the diseased site while ignoring healthy tissue, do its job and then exit the body. Unfortunately, this rarely occurs since even if the drug is able to pass through the required membrane, it still may not reach its desired destination due to the fact that a drug, unless directly injected into the blood, must pass through a complex system of living cell membranes before it can enter the bloodstream. For example, chemicals that enter the digestive tract must be absorbed by the cells lining the small intestine and then transferred through the cell to the other side where the chemical can then be absorbed by the capillary cells into the blood stream. Many medications administered this way are never absorbed by the blood stream, because they are chewed up by the enzymes as they pass through the digestive system. If the drug does make it to the blood from the intestines, it may be broken down or altered by the liver. Factors such as these make it vital to understand how a drug will react to and affect certain parts of the body prior to use in the human body.

Initially, drugs were tested in Petri dishes, through modeling with computer programs, animal and humans testing, and despite this testing of many of these drugs, still have unforeseen side effects. This is because a drugs effect depends less on chemistry than on the way it navigates the obstacle course that encompass the human body. A drug often changes and evolves as it travels through the body, such as being broken down by the liver, absorbed by the intestines, or held onto by fat. Therefore, it is essential to monitor the progress of a drug as it moves through the organs and tissues, however it is difficult to rationalize conducting such preliminary tests on human subjects.

Currently methods of testing experimental drugs and chemicals include in vitro tissue and cell cultures; computer modeling of real-life situations used to make predictions about the toxicity of a substance and model the action of a drug in the body; and organs donated from organ donors artificially maintained for research purposes. Alternatively, and generally preferred for accuracy, is in vivo animal testing. Live animals are essential in research and testing because they reflect the dynamic interactions between the various cells, tissues and organs comprising the human body. Animal testing, however, poses obvious problems to researchers because it is an inaccurate model for human drug response. Also, the protests of animal rights activist groups are continuously pushing to ban animal testing all together. The number of animals needed for product safety development has been reduced greatly; however, many of the alternative means of testing are still in the development stage and cannot yet take the place of animal tests.

Recently, a cartridge has been developed in vitro that mimics the blood brain barrier (BBB) in vivo. The mammalian BBB is comprised of micro-vascular endothelial cells that act as a virtually impenetrable barrier, thus isolating the brain from systemic influences, while simultaneously providing a pathway for the transport of nourishment to neurons buried in the brain parenchyma. The selective permeability of the barrier plays a crucial role in regulating the trafficking that occurs between blood and the central nervous system. The cartridge grows endothelial cells in one or more hollow fibers contained in a sealed housing compartment. The endothelial cells are introduced to the hollow area of the fibers where they attach and grow. A pump regulates the flow of media that is introduced into the fiber, manipulating the amount pressure put on the cells. This method is unique because it grows the cells in the presence of chronic shear stress, or flow. This is an important factor in the development of endothelial cells; those cultured under chronic shear stress respond in a physiologic manner and form a monolayer, stop dividing, orient to the flow of medium and form tight junctions. Glial cells are then grown on the exterior of the fiber that secretes "permissive' or "promoting" factors further influencing the proper development of the endothelial cells. This system provides an environment that is more realistic to that which occurs in vivo than other methods, such as endothelial cells cultured in standard culture flasks. In flasks, cells continuously grow and divide, never expressing tight junctions or other indicators of normal, in vivo physiology.

Thus far, this method has only been applied to the blood brain barrier. Each organ membrane has unique characteristics and transport requirements, therefore it is vital to have tests that will determine what drugs can and cannot enter certain organs, and how these drugs effect and are affected by the organs they contact. Tests using real human cells and tissues of these various organs have been limited however, due to the difficulties of developing procedures and techniques for growth, maintenance, and testing of these tissues and cells, and of devices and methods, which when these tissues and cells are incorporated, realistically mimic the respective organ.

It is an object of the present invention to grow cells and tissues from human organs in and/or about at least one hollow fiber and to test the effect of chemical compounds and agents on the cells and tissue. It is another object of the present invention to provide a system for joining several cartridges in fluid connection and testing the effect the cells and tissues have on the chemical compound or agent, and what portion of the chemical compound or agent passes through each cell or tissue culture. Finally, it is another object of the invention to describe a method of mimicking the body systems by joining several cartridges together in fluid connection, such that the chemical compound or agent passes through the contained cell and tissue cultures in the same order it would in the body. Therefore, the present invention provides a method for testing the course of a drug in vitro that will monitor and take into account the effect each cartridge containing different types of cells and/or tissue has on the drug.

SUMMARY OF THE INVENTION

The present invention relates to joining two or more cartridges containing cell or tissue cultures from different organs found in the human body in fluid connection.

The present invention is vital for the advancement of science, research, and development of new chemicals and agents. Currently there is no in vitro method for testing chemicals and agents as they pass through organs other than the brain or combinations of body systems including the brain. This invention would greatly enhance the ability for researchers to test a proposed drug on human cells and tissue prior to testing it in vivo. Often, it is found that drugs have different reactions when tested on a single organ in vitro or in animals, than it does in the human body. The present invention eliminates the uncertainty many clinicians face when testing a drug for the first time in a human, and specifically helps the researcher or clinician predict the possibly harmful side effects or failure of desired effect.

One embodiment of the present invention, involves a cartridge system comprising at least two cartridges comprising cell and tissues cultures from various body organs in and or around at least one hollow fiber, fluidly connected in series. Media or solution comprising a chemical or agent is passed through the two or more cartridges to determine the amount of chemical or agent that is transported or absorbed through the cell or tissue layer. The media or solution comprising a chemical or agent that does not transport through the cell or tissue layer is pumped into the next cartridge in the series.

Another embodiment of the present invention, involves a multiple cartridge test system capable of testing the cumulative effect of transport of a chemical or agent over various types of cells or tissue cultures from a different organs found in the human body. In this embodiment, a solution comprising a chemical or agent is introduced into the first cartridge in the series, and the chemical or agent that is transported through the cell or tissue layer is passed into the next cartridge in series. This embodiment allows for the testing of both the effect a chemical or agent has on cells and tissues, and also the effect cells and tissues may have on a chemical or agent. Often times a chemical or agent may be beneficial to one type of cells or tissue, but toxic to others.

In yet another embodiment of the present invention, a multiple cartridge test system contains a combination of cartridges in both parallel and serial connection. Connecting cartridges in parallel more effectively mimics the affect an organ would have on a chemical or agent, because it allows the chemical or agent exposure to a greater amount of cells and tissue, similar to organs found in the human body.

The present invention relates to a method of testing the affect of chemicals or agents on two or more cartridges types of cells or tissues. This method comprises the steps of assembling two or more cartridges comprising at least one hollow fiber, the hollow fiber of each cartridge comprising at least one layer of cell or tissue cultures and each cartridge being used for a different type of cell or tissue culture; joining the two or more cartridges in fluid connection such that a solution exiting one cartridge enters the next; and testing a chemical or agent in solution through the set of cartridges to determine what portion of the chemical or agent passes through each different type of cell or tissue The present invention further relates to a method of testing chemicals or agents on two or more types of cells or tissues joined in the same succession found between at least two organs of the human body. This method comprises the steps of assembling two or more cartridges comprising at least one hollow fiber, the hollow fiber of each cartridge comprising at least one layer of cell or tissue cultures and each cartridge being used for a different type of cell or tissue culture; joining the two or more cartridges in fluid connection such that a solution exiting one cartridge enters the next; and testing an chemical or agent in solution through the set of cartridges to determine how the drug is absorbed, how it changes, and how it affects cell or tissue cultures as it travels through the body systems.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DESCRIPTION OF THE PREFERRED EMBODIMENT

Figure 1:
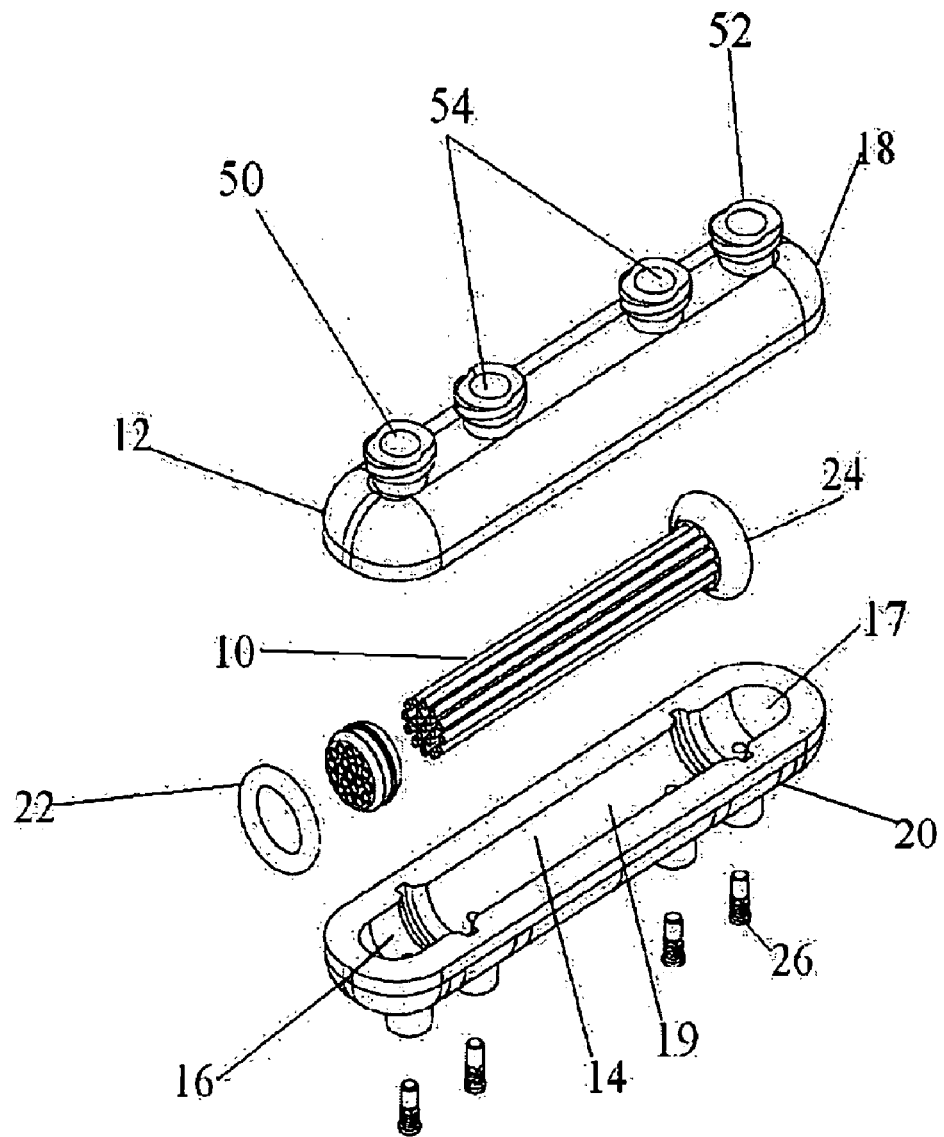
FIG. 1. Side exploded view of a cartridge of the present invention.

Referring now to the drawings, the illustrations are for the purpose of describing the preferred embodiment of the present invention and are not intended to limit the invention as described herein. The present invention relates to a cartridge system containing cell or tissue cultures (not shown) and a method of testing the affect of chemicals or agents on two or more types of cells and tissues. The cartridge system provided in the present invention preferably consists of two or more cartridges 12 in fluid connection and is exemplified by a number of embodiments as further described in the application. The method of the present invention is also further exemplified by a number embodiments described in the application.

FIG. 1 is a side exploded view of one embodiment of the cartridge 12 of the present invention. The cartridge 12 comprises at least one hollow fiber 10 running through a portion 14 or through the entire length of the cartridge; the hollow fiber 10 running through the cartridge 12 being used to transport a solution comprising an chemical or agent to be tested (not shown).

The cartridge 12 provided is a three dimensional housing structure and may be comprised of one or more chambers 14, 16, 17. Preferably, the cartridge 12 is designed such that media containing a chemical or agent can flow through the hollow fiber 10 containing epithelial cells (not shown), and any chemical or agent which is transported across the epithelial cells can be measured from the chamber 14, 16, 17 or other containment device which surrounds the hollow fiber 10. One such embodiment of the cartridge preferably consists of the three chambers 14, 16, 17; separated by sealable inserts 22, 24. The sealable inserts 22, 24 are preferably sealed to the bottom section of the cartridge 20, with one or more fibers 10 extending the length the two inserts 22, 24, connecting the first and third chambers 16, 17 respectively with the second chamber 14. The second chamber 14 comprises the hollow fiber 10. The three chamber cartridge consists of two half sections, a top section 18 and bottom section 20; fused together to form the cartridge. The housing of the cartridge is preferably made of polycarbonate; however, any suitable material may be used that is capable of sterilization. The three chambered cartridge preferably consists of at least three ports 50, 52, 54. The input port 50 introduces fluid into the chamber 16 leading to the hollow fibers 10. The output port 52 is fluidly connected with the end chamber 17 opposite the input port 50 and chamber 16. The cartridge 12 may also contain one or more sampling ports 54 for testing purposes.

Another embodiment of the cartridge 12 of the present invention is a single chamber cartridge (not shown). The single chamber cartridge (not shown) preferably consists of an input port and an output port in direct fluid connection with a hollow fiber. The single chamber cartridge preferably also contains one or more sampling ports for testing purposes Various embodiments of the cartridge of the present invention preferably include a bottom panel 20 that may consist of at least three electrodes 26 connected to each of the chambers 16. The electrodes 26 allow for trans-endothelial electrical resistance (TEER) measurement in a practical and economical manner, including the ability to measure the impedance at various frequencies. The electrodes 26 may be used for other purposes based on the goal of the experiment.

As depicted in FIG. 1, preferably, the hollow fibers 10 are first assembled into the two sealable inserts 22, 24 by either attaching them adhesively, holding them through compression fitting, or by some other method known to those skilled in the art. The two sealable inserts 22, 24 with the fibers 10 are then preferably introduced into slots created in the top 18 or bottom 20 sections of the cartridge 12. Then preferably, the top 18 and bottom 20 sections of the cartridge 12 are brought together and mechanically or adhesively attached (not shown). Preferably, they are attached using a UV-cure adhesive, and the adhesive is cured using a UV-light source. However, it is envisioned that the top 18 and bottom 20 sections, however, can be attached utilizing any suitable attachment means known in the art including the use of threaded fasteners, hinge and latch combination, snap fit connection, etc (not shown). Further, the hollow fibers 10 may be removable in embodiments where the cell or tissue cultures were to be examined.

It is also envisioned that the cartridge 12 can be of a number of other configurations. Any configuration set forth in this application can be assembled as mentioned above or by any other technique known to those skilled in the art. If for example a single chamber cartridge is used, instead of having inlet and outlet chambers 16, 17 the cartridge 12 would have direct connections to the hollow fiber(s) 10 on either end of the chamber. It is also envisioned that a two chamber cartridge could be used where the cartridge has either an inlet or outlet chamber, but not both.

The cartridge 12 also preferably has at least one port 50, 52, 54 or another means for injecting media and cells (not shown) into the chamber surrounding the hollow fiber(s) 10 and for withdrawing samples (not shown) from this chamber 17. In assembling the cartridge, care needs to be given making sure such ports or other means can be sealed to prevent contamination in the chamber 14, 16, 17 and also to prevent leakage of solution or media.

The hollow fibers 10 of various embodiments of the present invention need not only to be hollow transversely, but also the fiber itself needs to be porous to allow for fluid in the inside of the fiber to transport across the skin of the fiber. Preferably, the hollow fibers 10 skin is porous enough to allow media which makes it through the cells grown on the inside of the hollow fiber 10 to readily escape through the skin of the fiber, but have a small enough pore size to prevent cells from moving through the pores or growing substantially into the pores. Suitable hollow fibers 10 provide optimal combination of such properties as gas permeability, strength, porosity, selectivity and biocompatibility. Preferably, the molecular weight of the material the fiber is produced from is from about 1 kD to about 1,000 kD. The walls of the fibers 10 preferably include a plurality of pores between about 0.01 µm and about 0.64 µm. Preferably, the inner diameter for each hollow fiber 10 is between 510 µm and 690 µm, and each provides a wall thickness of between about 2 µm and 200 µm. The quantity of hollow fibers 10 can be as few as one to more than twelve depending on the limitations of the housing. The hollow fiber(s) 10 traverse the length of the cartridge 12 between the inlet port 50 and outlet port 52 and can be bundled together in any suitable fashion or combination.

Preferably, the skin of the hollow fibers 10 is formed of a polymer material. By way of example but not limitation, the hollow fibers can be formed from polypropylene, polyester, polystyrene, polycarbonate, nitrocellulose compound, polyethylene, polysolfone, cellulose, polymethyl methacrylate, polyacrylonitrile, polyvinylidne fluoride, and combinations thereof. The exterior periphery of the bundled hollow fibers 10 is separated from the inner walls of the housing and between themselves to accommodate cell growth. The fibers 10 are suspended and secured in the inlet 50 and outlet port 52 when using a single chamber cartridge preferably by a medical grade epoxy adhesive. The adhesive also seals any gaps in the ports so there is no leakage in the cartridge 12. The hollow fibers 10 may be suspended using other suitable sealing means, so long as the sealing means provides a durable, waterproof, and watertight seal yet retains the structural integrity of the housing. Such means include, but are not limited to use of adhesive silicon glue and various potting materials.

Polypropylene, the most preferable material used for the fibers 10, is in and of itself a poor substrate for cellular attachment and thus requires the application of a suitable matrix material or compatibility layer prior to using it for successful cell culture. Prior to a treatment application of such matrix material or compatibility layer, the fibers are preferably rinsed with ethanol to reduce hydrophobic interactions prior to use as a semi-permeable membrane.

The hollow fibers 10 contained by the cartridge 12 will be used to transport solution comprising a chemical or agent. The solution is preferably a composition, which not only allows the cells and tissue to survive and more preferably thrive, but is of a composition which mimics or resembles an animal's (and most preferably a human's) blood stream (not shown). One example of a solution that may be used with the method and cartridge of the present invention consists of growth media comprised of bulk ions (Na, K, Ca, P, bicarbonate or $CO_2$), trace elements (iron, zinc, selenium), sugars, amino acids, vitamins, choline, serum (which may contain a large number of growth promoting activities such as buffering toxic nutrients by binding them, neutralizes trypsin and other proteases, has undefined effects on the interaction between cells and substrate, and contains peptide hormones or hormone-like growth factors that promote healthy growth), and antibiotics (not required for cell growth, however used to control growth of bacterial and fungal contaminants).

The specific chemical or agent is dependant on the goal of the experiment and the type of cells involved. The cartridge 12 and method of the present invention may be used to test the affect of various chemicals and agents on various cell or tissue barriers in an animal's body. For example, one might test the effect of a chemical or agent on the blood brain barrier. In one application, the chemical or agent might be tested to make sure that it isn't passing through the blood brain barrier. In another application, the chemical or agent may be tested conversely to make sure it is passing through the blood brain barrier.

Preferably, when testing, the chemical or agent (not shown) will be of known concentration; and sampling of the extracapillary space 19 will provide information on the permeability of said chemical or agent across each capillary wall containing grown tissue and/or cells. Such chemicals and agents may include but are not limited to drugs, chemicals, metabolic bi-products, poisons, toxins, herbs, proteins, vitamins, minerals, other cells, and the like.

A second cell suspension optionally may be added to the extracapillary space 14 using a process similar to loading of the intercapillary spaces (not shown), except that the flow may be continued through the hollow fibers 10 during the entire process. The second cell suspension is preferably used to allow scientists or clinicians to better mimic or resemble various organs or tissues as described earlier. For example, with the blood brain barrier the second cell suspension to be grown in the extra-capillary space 19 may be glial cells. Still optionally, other layers of cells may be grown over the extra-capillary layer to still more preferably better mimic or resemble the various organs or tissues of the animal.

The cells and tissues contained in or about the hollow fiber(s) 10 of the cartridge system are preferably those found in organs of the human body. Such organs include, but are not limited to the heart, lungs, stomach, liver, intestines, kidneys, gull bladder, bladder, spleen, and pancreas. Various embodiments of the multiple cartridge test system preferably include combinations of two or more different cell or tissue cultures in fluid connection. It is a further embodiment of the multiple cartridge test system of the present invention that preferably, the solution comprising a chemical or agent is run through the system consisting of different cell and tissue cultures to test the effect of the chemical or agent on the two or more cartridges 12.

Various embodiments of the present invention include a system of two or more cartridges 12 comprising cell or tissue cultures from different organs found in the human body (not shown), and a method for testing chemicals or agents on such system. Other embodiments of the present invention involve a method of testing the affect of chemicals or agents on two or more types of cells or tissues. The method preferably comprises the steps of assembling two or more cartridges comprising at least one hollow fiber, the hollow fiber of each cartridge comprising at least one layer of cell or tissue cultures and each cartridge being used for a different type of cell or tissue culture; joining the two or more cartridges in fluid connection such that a solution exiting one cartridge enters the next; and testing a chemical or agent in solution through the set of cartridges to determine what portion of the chemical or agent passes through each different type of cell or tissue. The method of the present invention is further exemplified by various embodiments described in the application.

Figure 2:
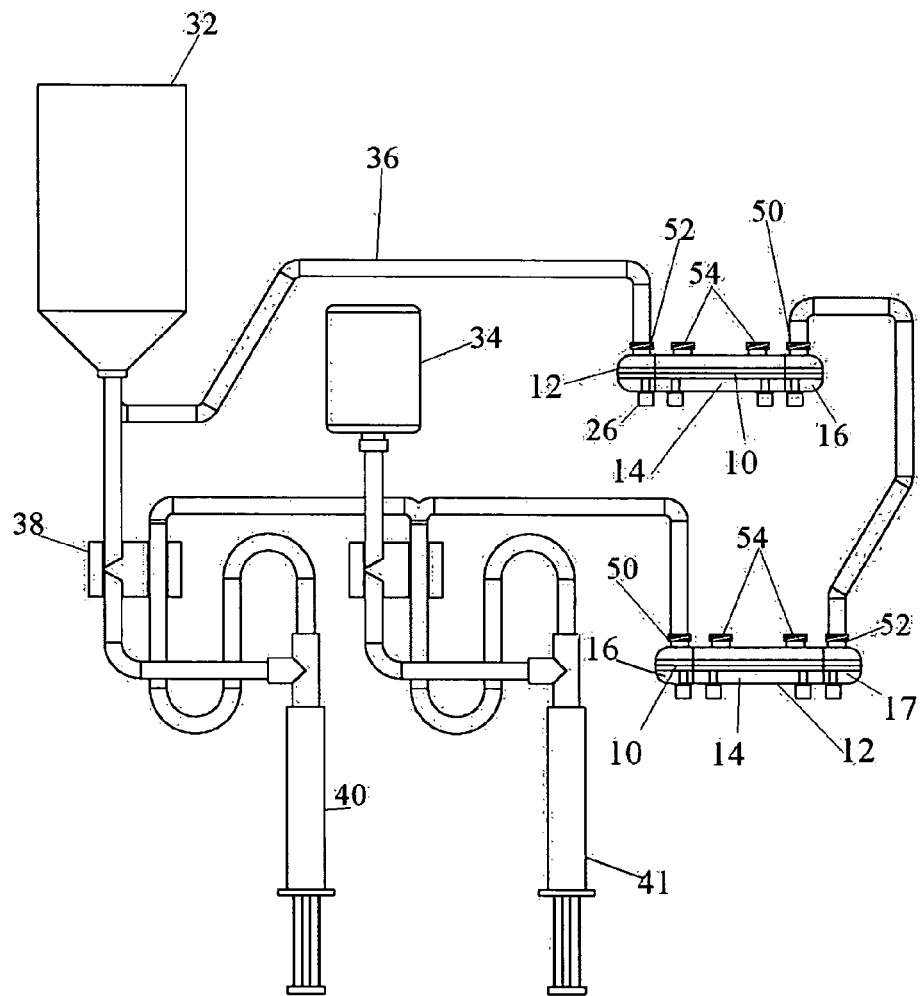
FIG. 2. Multiple cartridge test system comprising two cartridges in serial connection.

FIG. 2 represents one embodiment of a cartridge system in which two (or more) cartridges 12, similar to those described in FIG. 1, are connected in series. In this embodiment, the cartridges 12 are in fluid connection and comprise a testing system in which solution comprising a chemical or agent is passed through the hollow fibers 10 of each cartridge 12 in series. In this embodiment, a pump(s) 40 pulls solution from a reservoir 32 and pushes it through a system of gas permeable connective tubing 36. Preferably a second pump pulls a chemical or agent from a reservoir 34 and pushes it through the connective tubing where it may mix with the solution or media. Any number of pumps 40, 41 may be used depending on the number of chemicals or agents being tested. The pump 40, 41 is preferably a variable-speed pulsatile pump that generates flow from the solution reservoir 32 through the hollow fibers 10 of the cartridge(s) and back to the solution reservoir 32 through the connective tubing 36. Depending on the goals of the test, the strength and the speed of the pump 40 can be adjusted. Preferably, the strength and speed of the pump 40 is comparable to the heart, thus mimicking body conditions. Although the preferred tubing 36 is to fit $5/16$" connectors, the optimal dimensions of the tubing can be determined on a case by case basis. Preferably, the system contains pumps or valves, such as the valve 38 shown, ensuring controlled release of media or solution and chemical or agent.

The media or solution comprising a chemical or agent (not shown) is preferably introduced into the input port 50 of the first cartridge 12 in the system. Preferably, the solution comprising a chemical or agent (not shown) presented into the first cartridge 12 in the system travels through the hollow fibers 10 and a portion of the chemical or agent is transported through the cell or tissue layer (not shown), depending on the transport characteristics of the chemical or agent with respect to the cells or tissue being tested. Preferably, any chemical or agent not transported through the cells or tissue layer of the hollow fibers 10, is carried out of the cartridge 12 via the output port 52 and into the input port 50 of the next cartridge 12 in the series. Preferably the output port 36 of the last cartridge 12 in the system may then be connected to the beginning of the system and the remaining chemical or agent can be reintroduced (as shown in FIG. 2), allowing for timed studies of various chemical or agents with respect to two or more tissue or cell types Alternatively, the remaining chemical or agent can be collected from the output port 52 of the last cartridge 12 in the system and measured (not shown).

A practical example of this embodiment would be a multi-cartridge test system comprised of cartridges containing cell and tissue cultures from various organs believed to absorb and transport these type of chemicals or agents that such as, for example, the kidneys, liver, pancreas, heart, lungs, and the like. When a chemical or agent comes into contact with such organs, it is absorbed or transported into the organ due to a variety of factors. When administering a chemical or agent into the body, it is important to know the absorption rate of such organs to ensure the proper amount of chemical or agent reaches its ultimate or desired destination.

Figure 3:
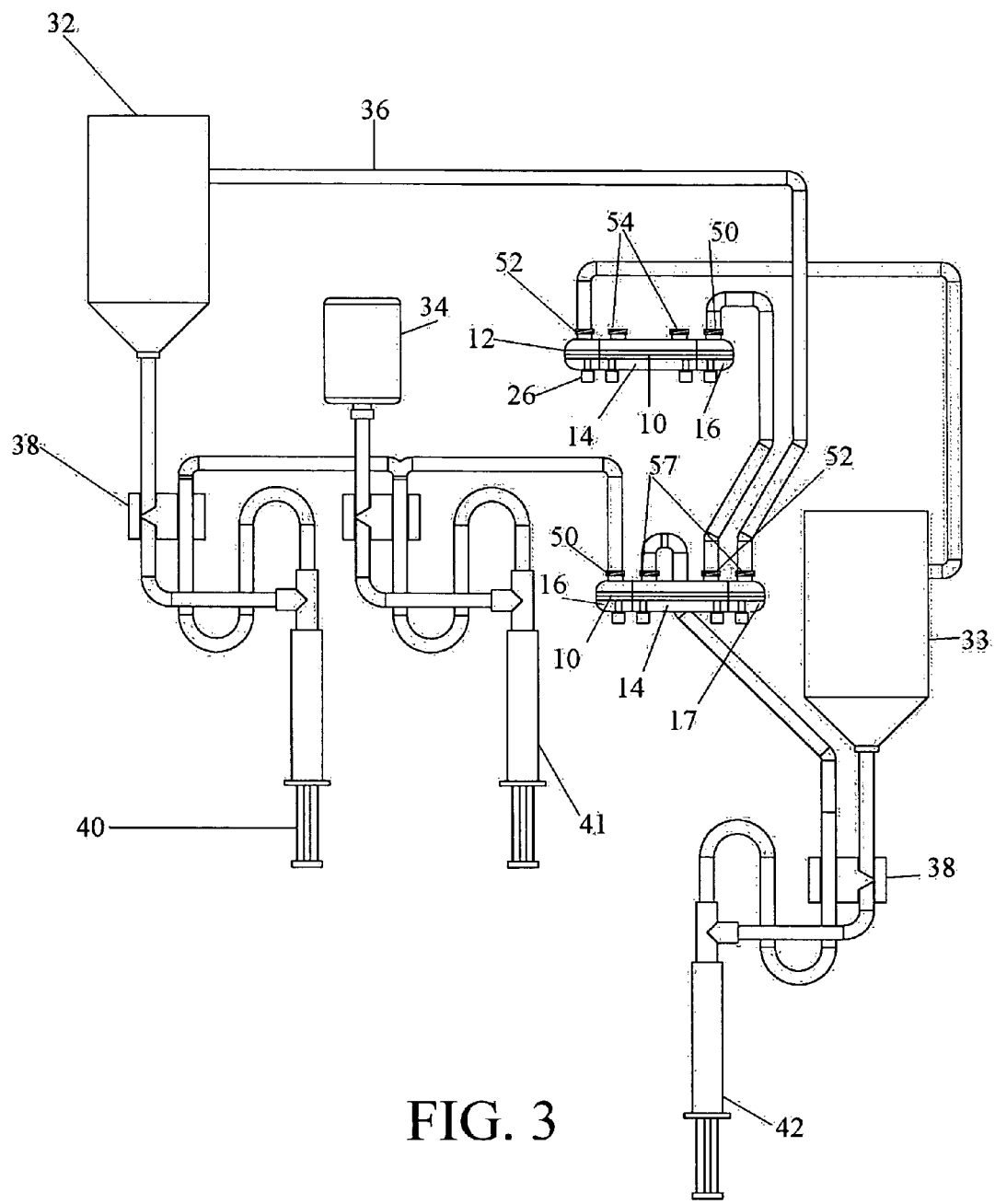
FIG. 3. Multiple cartridge test system which is capable of testing the cumulative effect of transport of a chemical agent over two or more types of cells or tissue cultures.

FIG. 3 represents another embodiment of the method of testing the affect of chemicals or agents on two or more types of cells or tissues in a cartridge system that tests the cumulative effect of a transport of a chemical or agent over two or more types of cells or tissue cultures. This system is similar to FIG. 2; however cartridges are fluidly connected in such a way that the media or solution carrying a chemical or agent that is transported across the hollow fiber 10 of one cartridge 12 is passed into the intercapillary space of the next cartridge 12. In order to ensure constant flow through the intracapillary space of this cartridge, a separate pump 42 and solution reservoir 33 can pump media or solution into the port connected to the intracapillary space of the first cartridge 57. The solution comprising a chemical or agent that does not transport through the hollow fiber of the second cartridge in the system is preferably circulated back to the solution reservoir 33. Alternatively, the solution comprising a chemical or agent may be removed and tested. The solution comprising a chemical or agent that does not transport through the cell or tissue layers of the first is preferably cycled back into the main solution reservoir 32, or collected for testing. Preferably, the cartridges 12 are arranged to mimic the human body, such that a solution comprising an chemical compound and agent travels through the tissues as it would in body systems such, The first cartridge representing a type of blood filtering organ such as the liver or kidneys, and the second representing an organ where ultimately the chemical or agent is to be delivered.

Most drugs exert effects on several organs or tissues, and have both unwanted side effects as well as desired therapeutic effects. There is no guarantee that the concentration and composition of a drug or chemical introduced into the body will be functional at the desired site. Often, as drugs or chemicals contact cells and tissues they are altered due to metabolism, absorption, excretion, etc. Therefore, the present invention is vital to test the interaction drugs and chemicals will have when in contact with such cells and tissues. FIG. 3 represents a system of testing not only the concentration of a chemical or agent that does not transport through the cell and tissue layers, but also the composition of the chemical or agent after it transports through the cell or tissue layer.

The present invention further relates to a method of testing the affect of chemicals or agents on two or more types of cells or tissues joined in the same succession found between at least two organs of the human body. This method preferably comprises the steps of assembling two or more cartridges comprising at least one hollow fiber, the hollow fiber of each cartridge comprising at least one layer of cell or tissue cultures and each cartridge being used for a different type of cell or tissue culture; joining the two or more cartridges in fluid connection such that a solution exiting one cartridge extracapillary space enters the intercapillary space of the next cartridge; and testing an chemical or agent in solution through the set of cartridges to determine how the drug is filtered, absorbed, how it changes, and how it affects cell or tissue cultures as it travels through the body systems. This method is further exemplified by various embodiments described in this application.

Figure 4:
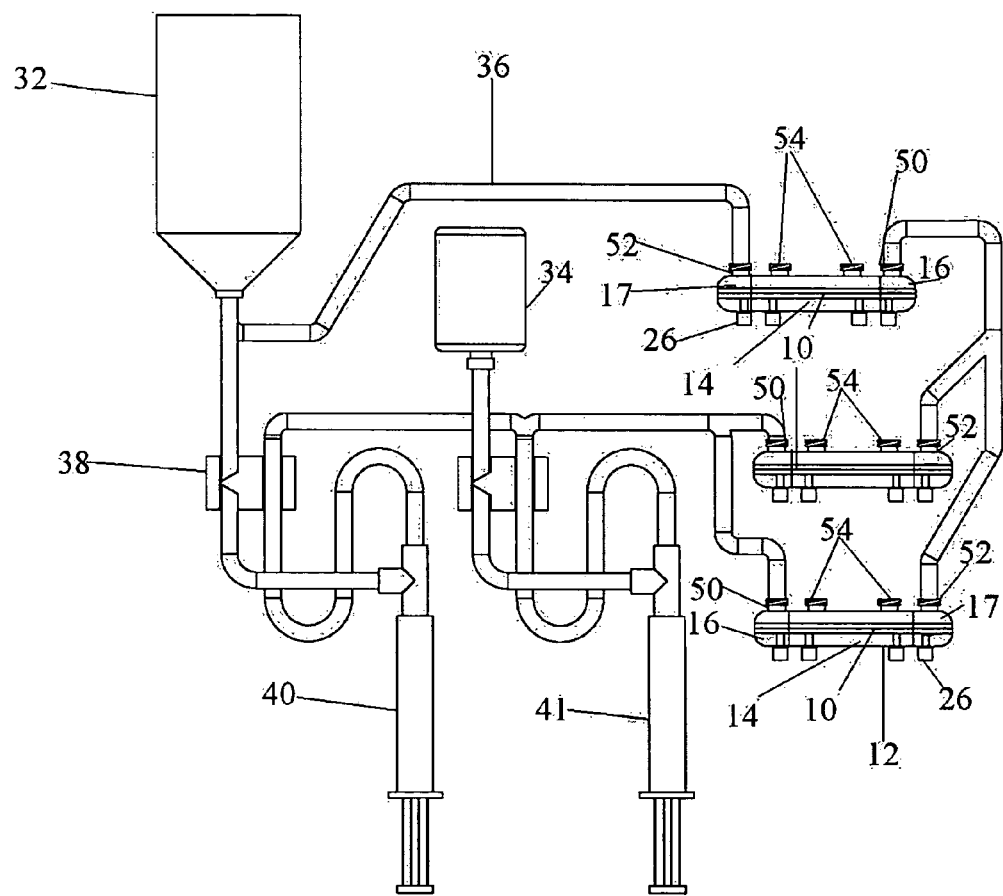
FIG. 4. Multiple cartridge test system with a combination of cartridges in both parallel and serial connection.
Figure 5:
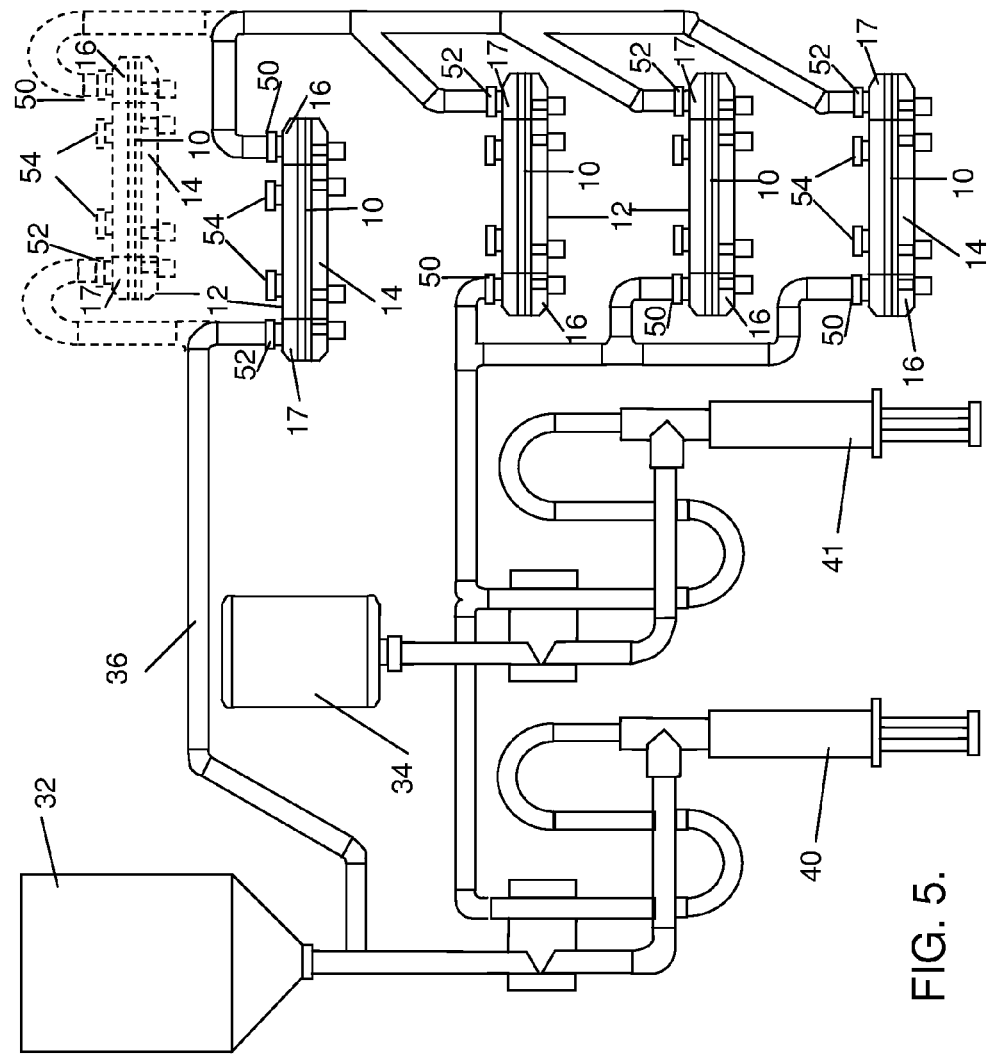
FIG. 5. Multiple cartridge test system with a combination of at least four cartridges with at least two in serial connection.

FIG. 4 represents a multiple cartridge test system with a combination of cartridges 12 in both parallel and serial connection. In this embodiment, solution is pulled from a solution reservoir 32 by a pump 40, and it is mixed with a chemical or agent that has been pulled from a reservoir 34 by pump 41. The solution comprising a chemical or agent (not shown) is then preferably passed thought connective tubing 36 into both of the two cartridges 12 connected in parallel. The solution comprising a chemical or agent that does not transport through the hollow fibers lined with cells or tissue is then passed into the input port 50 of another cartridge connected in series. The remaining solution is then preferably cycled back into the system or removed and measured (not shown). The number and/or combination of cartridges depend on the type of body system the test is mimicking. For example, if the target of a biological or chemical agent is the kidneys, the chemical or agent will likely contact other organs such as the stomach, liver, or the intestines as well. Therefore, by connecting cartridges containing cells or tissues from such organs in parallel and then serial connection with a cartridge containing cells or tissue from a kidney, the kidney will be exposed to a chemicals or agents that may be diluted or altered in some way that will have a different effect on the kidney than it would otherwise. Other embodiments may include numerous parallel and or serial cartridges in the system. Cartridges can be added in many combinations to mimic the transport characteristics of various organs. For example, 10 cartridges 12 containing one type of tissue could be used if it is determined that this was the number needed based on the configuration of the system to mimic a particular organ and to transport characteristics revealed to a particular set of chemicals or agents FIG. 5 represents a multiple cartridge test system with a combination of cartridges 12 in both parallel and serial connection. In this embodiment, solution is pulled from a solution reservoir 32 by a pump 40, and it is mixed with a chemical or agent that has been pulled from a reservoir 34 by pump 41. The solution comprising a chemical or agent (not shown) is then preferably passed thought connective tubing 36 into each of the cartridges 12 connected in parallel. In the currently represented embodiment, there are three such cartridges 12 connected in parallel, though there may be as few as two such connected cartridges. The solution comprising a chemical or agent that does not transport through the hollow fibers lined with cells or tissue is then passed into the input port 50 of those cartridges 12 which are connected in series. In the presently represented embodiment, there is one cartridge 12 connected in series with the previous three cartridges 12, but more may be attached as represented by the cartridge 12 comprising dashed lines. Similarly, additional cartridges 12 may be added (not shown) in parallel to either set or series of cartridges 12 connected in series with each other. The remaining solution is then preferably cycled back into the system or removed and measured (not shown). The number and/or combination of cartridges depend on the type of body system the test is mimicking. For example, if the target of a biological or chemical agent is the kidneys, the chemical or agent will likely contact other organs such as the stomach, liver, or the intestines as well. Therefore, by connecting cartridges containing cells or tissues from such organs in parallel and then serial connection with a cartridge containing cells or tissue from a kidney, the kidney will be exposed to a chemicals or agents that may be diluted or altered in some way that will have a different effect on the kidney than it would otherwise. Other embodiments may include numerous parallel and or serial cartridges in the system. Cartridges can be added in many combinations to mimic the transport characteristics of various organs. For example, 10 cartridges 12 containing one type of tissue could be used if it is determined that this was the number needed based on the configuration of the system to mimic a particular organ and to transport characteristics revealed to a particular set of chemicals or agents.

The cartridge 12 provided is a three dimensional housing structure and may be comprised of one or more chambers 14, 16, 17. Preferably, the cartridge 12 is designed such that media containing a chemical or agent can flow through the hollow fiber 10 containing epithelial cells (not shown), and any chemical or agent which is transported across the epithelial cells can be measured from the chamber 14, 16, 17 or other containment device which surrounds the hollow fiber 10. One such embodiment of the cartridge preferably consists of the three chambers 14, 16, 17. The three chambered cartridge preferably consists of at least three ports 50, 52, 54. The input port 50 introduces fluid into the chamber 16 leading to the hollow fibers 10. The output port 52 is fluidly connected with the end chamber 17 opposite the input port 50 and chamber 16. The cartridge 12 may also contain one or more sampling ports 54 for testing purposes.

Another embodiment of the present invention involves testing the actual cells or tissue cultures after exposure to the chemical or agent. Preferably, after a solution comprising a chemical or agent has been tested on a multiple cartridges testing system, the actual cells or tissue cultures are removed from the cartridges 12 and examined. Preferably, the hollow fibers 10 are easily removed from the cartridges 12 to ensure the cells or tissue is not damaged. The cell and tissue cultures are examined to test the effect a chemical or agent had on the cells or tissue. Often, a chemical or agent that is beneficial to one type of cell or tissue culture may be toxic to another. Further, it is important to know how a chemical or agent my affect cells or tissue because some chemicals or agents may chemically alter or mutate cells that could be detrimental to a body system.

Further embodiments of the present invention involve the use of various types of cells in the hollow fibers 10 other than epithelial cells. When a chemical or agent is introduced into the body, it can interact with stem cells, the daughters or progenitor cells of the stem cells that provide the bulk of the tissue, and the highly specialized or differentiated cells. These cells do not all react the same way to a biological or chemical agent. That which is beneficial to some cells may be toxic to others. Particularly, stem cells are very susceptible to outside influence, since they need a signal to turn on certain genes and differentiate. Also, current evidence indicates that some stem cells are involved in assisting cancer's proliferation. Therefore, knowing if the chemical or agent specifically alters embryonic or adult stem cells is very important Preferably, the system of the present invention comprises at least two cartridges; more preferably, comprises at least three cartridges; even more preferably, comprises at least four cartridges, and most preferably, comprises at least six cartridges. Preferably, the system of the present invention can be configured to represent varying sized organs. When representing various sized organs, this can be done either by changing the dimensions of the cartridges or by adding and subtracting any number of cartridges with the same tissue and/or cells to represent smaller and larger organs. Preferably, the system also includes additional pumps and/or valves for the testing of at least two biological or chemical agents simultaneously, more preferably for the testing of at least three biological or chemical agents simultaneously and most preferably for the testing of at least four biological or chemical agents simultaneously.

In addition, the system of the present invention can further preferably includes a heater or method of heating the media and cartridges to better simulate the actual living conditions of the tissues and/or cells, an analytical device for measuring the composition of the media or fluids at various points in the system, and/or injection system or method for replacing or regenerating the media being circulated through the system.

Preferably, various sensors are placed at different points within the system to allow for analysis or regeneration of the media. The signal from these sensors would be feed to a controller for example a processor, chip or computer, which depending on the signal might either cause a valve to open or a pump to operate injecting new media, chemicals or agents into the system or simply record the data. The sensors might also be used to record the condition of the cell or tissue layers in the cartridges, and to shut the experiment down if one or more of these layers have failed.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of testing the affect of chemicals or agents on two or more types of cells or tissues comprising the steps of:
    assembling two or more cartridges comprising at least one hollow fiber, the hollow fiber of each cartridge comprising at least one layer of cell or tissue cultures and each cartridge being used for a different type of cell or tissue culture;
    joining the two or more cartridges in fluid connection such that a solution exiting one cartridge enters the next;
    testing a chemical or agent in solution through the set of cartridges to determine what portion of the chemical or agent passes through each different type of cell or tissue.

2. The method of claim 1, wherein the cartridges comprise a combination of at least two human cell or tissue cultures from the group consisting of organs consisting of heart, lungs, stomach, liver, intestines, kidneys, gull bladder, bladder, spleen, appendix, brain, and pancreas.

3. The method of claim 1, wherein steps are used to test at least two chemicals and/or agents simultaneously.

4. The method of claim 1, wherein at least three cartridges are used.

5. The method of claim 1, wherein at least two of the cartridges in the system are in parallel connection.

6. The method of claim 1, wherein the method uses at least four cartridges and at least two of the cartridges in the system are in serial connection.

7. A method of testing the affect of chemicals or agents on two or more types of cells or tissues joined in the same succession found between at least two organs of the human body comprising the steps of
    assembling two or more cartridges comprising at least one hollow fiber, the hollow fiber of each cartridge comprising at least one layer of cell or tissue cultures and each cartridge being used for a different type of cell or tissue culture;
    joining the two or more cartridges in fluid connection such that a solution exiting one cartridge enters the next;
    testing a chemical or agent in solution through the set of cartridges to determine how the drug is absorbed, how it changes, and how it affects cell or tissue cultures as it travels through the body systems.

8. The method of claim 7, wherein at least one of the cartridges comprise kidney or liver cells and/or tissues.

9. The method of claim 7, wherein the cartridges comprise a combination of at least two human cell or tissue cultures from the group consisting of organs consisting of heart, lungs, stomach, liver, intestines, kidneys, gull bladder, bladder, spleen, appendix, brain, and pancreas.

10. The method of claim 7, wherein at least one of the cartridges comprise human cells or tissues from the group consisting of cells or tissues from the digestive system including the esophagus, stomach, liver, pancreas, and intestines, mimicking the passage of orally administered chemicals or agents.

11. The method of claim 7, wherein at least one of the cartridges comprise human cells or tissues from the group consisting of cells or tissues from the respiratory system including the lungs, trachea, and diaphragm, mimicking the passage of inhaled drugs or chemicals.

12. The method of claim 7, wherein at least one of the cartridges comprise human cells or tissues from the group consisting of cells or tissues from the excretory system including the lungs, kidneys, and the bladder.

13. The method of claim 7, wherein at least one of the cartridges comprise human cells or tissues from the group consisting of cells or tissues from the circulatory system including the heart, and blood vessels, mimicking the passage of injected drugs or chemicals.

14. The method of claim 7, wherein the method uses at least four cartridges with at least two of the cartridges in parallel connection and at least two of the cartridges in serial connection.

* * * * *

UNITED STATES PATENT AND TRADEMARK OFFICE
CERTIFICATE OF CORRECTION

| | | |
|---|---|---|
| PATENT NO. | : 7,943,371 B1 | Page 1 of 1 |
| APPLICATION NO. | : 11/546704 | |
| DATED | : May 17, 2011 | |
| INVENTOR(S) | : Edward J. Rapp | |

It is certified that error appears in the above-identified patent and that said Letters Patent is hereby corrected as shown below:

On the Title Page, Item (54),
Delete "SYSTEM AND TESTING BIOLOGICAL AND" and insert -- SYSTEM FOR TESTING BIOLOGICAL AND --.

Column 1,
Line 1, delete "SYSTEM AND TESTING BIOLOGICAL AND" and insert -- SYSTEM FOR TESTING BIOLOGICAL AND --.

Signed and Sealed this
Twenty-eighth Day of February, 2012

David J. Kappos
*Director of the United States Patent and Trademark Office*